United States Patent [19]
Plecha et al.

[11] Patent Number: 6,087,405
[45] Date of Patent: Jul. 11, 2000

[54] TITANIA CATALYSTS, THEIR PREPARATION AND USE IN FISCHER-TROPSCH SYNTHESIS

[75] Inventors: Stanislaw Plecha, Columbia, Md.; Charles H. Mauldin, Baton Rouge, La.; Larry E. Pedrick, Houston, Tex.

[73] Assignee: Exxon Research and Engineering Company, Florham Park, N.J.

[21] Appl. No.: 09/348,890

[22] Filed: Jul. 6, 1999

Related U.S. Application Data

[62] Division of application No. 09/021,477, Feb. 10, 1998.

[51] Int. Cl.[7] .............................. C07C 27/00; C07C 27/06
[52] U.S. Cl. ................................................. 518/715
[58] Field of Search ............................................ 518/715

[56] References Cited

U.S. PATENT DOCUMENTS

| | | | |
|---|---|---|---|
| 4,992,406 | 2/1991 | Mauldin et al. ........................ | 502/304 |
| 5,140,050 | 8/1992 | Mauldin et al. ........................ | 518/715 |
| 5,215,953 | 6/1993 | Blumrichet et al. .................... | 502/218 |
| 5,348,982 | 9/1994 | Herbolzheimer et al. .............. | 518/700 |

FOREIGN PATENT DOCUMENTS

| | | | |
|---|---|---|---|
| 0266898 | 5/1988 | European Pat. Off. ......... | B01J 23/74 |
| 2070959 | 9/1981 | United Kingdom ............. | B01J 21/06 |

*Primary Examiner*—Steven P. Griffin
*Assistant Examiner*—Christina Ildebrando
*Attorney, Agent, or Firm*—Jay Simon

[57] ABSTRACT

Supports for Fischer-Tropsch catalysts with increased strength and attrition resistance are formed by incorporating both silica and alumina into a support comprised primarily of titania; whereupon Fischer-Tropsch active metals can be composited with the support; the catalysts being particularly useful in slurry reactions.

10 Claims, 1 Drawing Sheet

TITANIA CATALYSTS, THEIR PREPARATION AND USE IN FISCHER-TROPSCH SYNTHESIS

This is a division of application Ser. No. 09/021,477, filed Feb. 10, 1998.

FIELD OF THE INVENTION

This invention relates to titania containing supports, their preparation, and use as catalysts (with added metal(s)) for Fischer-Tropsch hydrocarbon synthesis. More particularly, this invention relates to material that can withstand the high water partial pressures often encountered in hydrocarbon synthesis processes, for example, slurry based processes.

BACKGROUND OF THE INVENTION

U.S. Pat. No. 5,140,050 describes improvements in the preparation of supports useful in the preparation of Fischer-Tropsch catalysts, and the unexpected results obtained from the use of these catalysts in the Fischer-Tropsch process. As useful as these improved catalysts and supports have been, the operating conditions for Fischer-Tropsch synthesis, particularly the relatively high water partial pressures that occur as a result of the Fischer-Tropsch reactions, have led to the weakening of the catalysts and the formation of excessive fines in the reaction mixture. The fines have several deleterious effects including the clogging of lines, reduced catalyst efficiency, and loss of catalyst through filters, as well as clogging of filters. Consequently, there is a need for the development of a catalyst that can retain its integrity—and thereby its efficiency—under steaming conditions such as are present during the Fischer-Tropsch process. In particular, the severity of slurry operations combined with the steaming conditions requires a catalyst of high attrition resistance.

SUMMARY OF THE INVENTION

In accordance with this invention, both silica and alumina are employed as binders for a titania containing support to achieve the integrity required of a catalyst used in Fischer-Tropsch synthesis. The catalyst is formed by dispersing one or more metals active for Fischer-Tropsch synthesis, e.g., Group VIII metals such as cobalt or ruthenium, over the surface of the support. Thus, a high-strength—as measured by attrition resistance—catalyst is formed that maintains its integrity under conditions of relatively high water partial pressure at elevated temperatures, e.g., 175–400° C., used in Fischer-Tropsch processes.

U.S. Pat. Nos. 5,140,050 and 4,992,406 disclose porosity improvements for titania containing supports by virtue of the use of alumina or zirconia or silica binder materials—in that order of preference. The invention described herein, however, discloses that the use of silica, a less preferred material than alumina as a binder, together with alumina, produces a titania containing material with greater attrition resistance, either in a dry state or under steaming conditions, than either alumina or silica alone. Consequently, there is a seeming anomaly in the fact that the addition of a less preferred material to a composition containing titania and alumina results in an even stronger support material.

The mechanism by which the synergy of alumina and silica produce high strength titania containing material is unclear. However, while not wishing to be bound by any particular mechanism, we theorize that in the finished, calcined support small silica particles occupy positions at the interface between larger alumina particles and much larger titania particles, and serve as a kind of chemical bonding agent. Thus, silica crystallites can partially merge with both alumina and titania crystallites to form an essentially continuous crystalline phase. The silica acts as a binding agent between the alumina and the titania, and the steaming either during calcination or Fischer-Tropsch synthesis, may further the formation of these mixed boundary phases of silica with alumina and silica with titania. Further, alumina by itself does not mix well with titania and only physical forces are relied upon to bind the particles. Steaming may well disrupt these physical forces, possibly by sintering the alumina and forming larger alumina particles that are less able to provide binding qualities. Silica by itself is not a good binder because of its affinity for titania which causes the silica to lose much of its separateness.

DESCRIPTION OF THE DRAWINGS

The FIGURE is a plot of the sonic attrition of various samples where the ordinate represents wt % fines of <25 microns and the abscissa is minutes in an ultrasonic bath. Curves A, B, C and D represent titania supports with steamed alumina, fresh alumina, steamed silica-alumina, and fresh silica-alumina binders, respectively.

DESCRIPTION OF PREFERRED EMBODIMENTS

Figure 1:
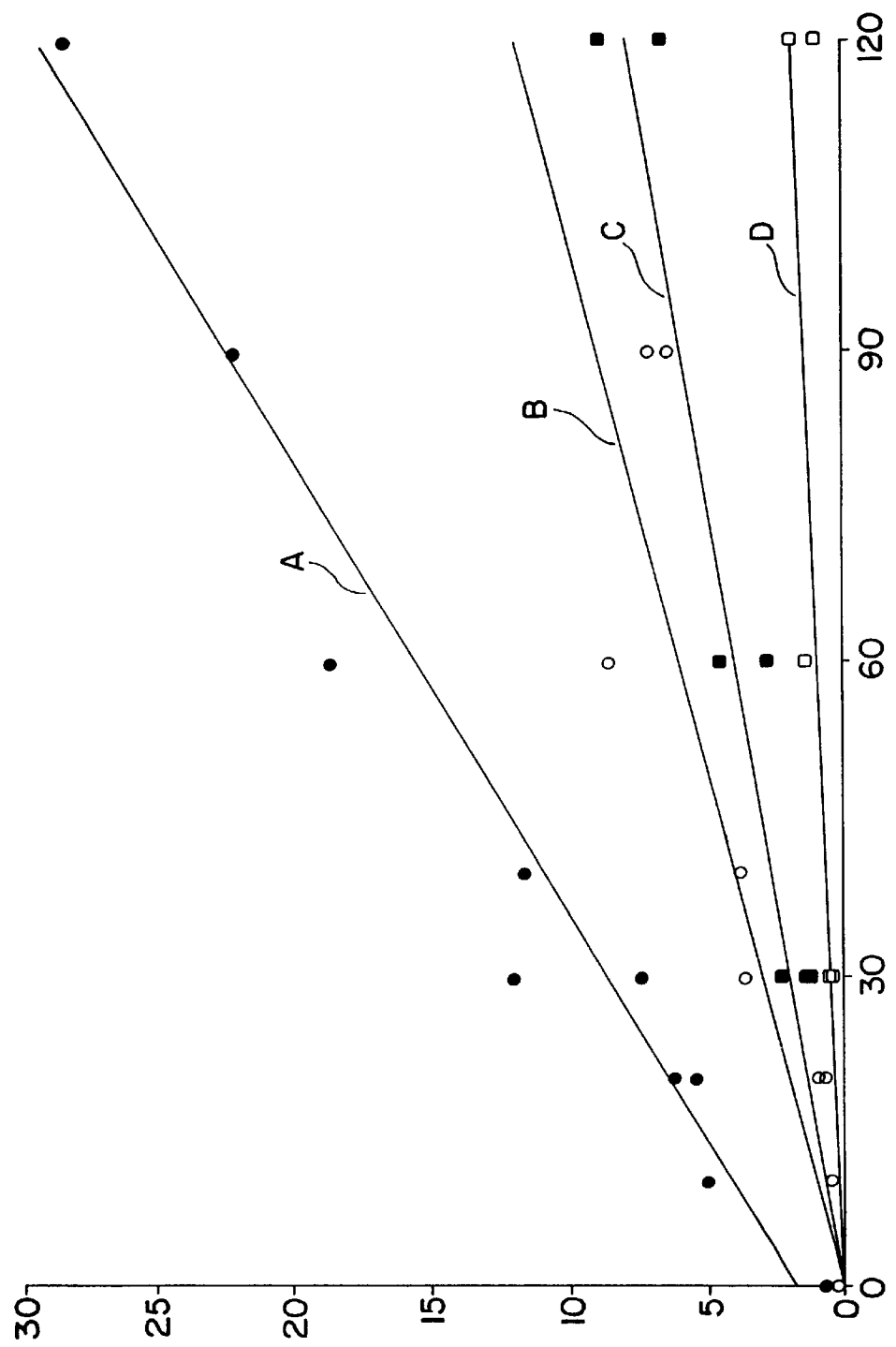

The titania containing support is a particulate material preferably containing at least about 50 wt % titania, more preferably at least about 80 wt % titania and preferably has a rutile:anatase ratio of at least about 1:9. This material is admixed with suitable amounts of silica and alumina acting as binder materials, where the binder makes up less than about 30 wt %, preferably less than about 20 wt %, more preferably about 3–20 wt %, still more preferably 4–15 wt %, yet more preferred 5–10 wt % of the total support. The silica and alumina binder mixture may contain 50 wt % or less silica, preferably about 3–50 wt % silica, more preferably 5–35 wt % silica.

The support is typically formed into porous particles with essentially spherical or cylindrical shapes by the well-known methods of extrusion, pilling, tableting, spray-drying, etc. A preferred method is spray-drying, in which a suitable aqueous slurry of titania and binder materials is atomized into a chamber purged with heated air. Spray-drying produces a spherical support with a size range of about 20 to 120 microns, which is well suited for use in slurry Fischer-Tropsch processes.

In order to achieve the benefits of porosity and strength, binder components are mixed with the titania starting material before the forming operation. They may be added in a variety of forms, as salts or preferably as colloidal suspensions or sols. For example, alumina sols made from aluminum chloride, acetate, or nitrate are preferred sources of the alumina component. Readily available silica sols are preferred sources of the silica component. In each case, however, care must be taken to avoid contamination of these binder sols by elements that are harmful to the active Fischer-Tropsch metals. For example, alkali and alkaline earth cations and sulfur-containing anions such as sulfate are potent poisons of cobalt under Fischer-Tropsch conditions, and hence must be minimized in preparing supports for cobalt catalysts.

Titania supports are typically calcined after forming in order to anneal the binders, and, optionally, to convert the anatase phase of titania to the rutile phase. This calcination is typically performed in air at temperatures ranging from 500 to 1000° C.

When preparing Fischer-Tropsch catalysts from this support, metals catalytically active for the Fischer-Tropsch synthesis are composited with the support. Preferred metals are those from Group VIII of the Periodic Chart of the Elements, particularly iron, cobalt and ruthenium, with cobalt and ruthenium being preferred and cobalt being most preferred. Promoters may also be employed such as zirconium, titanium, rhenium, hafnium, cerium, thorium and uranium, and others well known to those skilled in the art. The metal or metals are present in amounts that are catalytically active for Fischer-Tropsch synthesis and will vary with the metal being selected. For example, ruthenium is much more active in this environment than cobalt and, as a consequence is used in amounts ranging from about 0.5–3.0 wt % while cobalt will preferably be used in amounts of about 2–40 wt %, more preferably 5–30 wt %, still more preferably 10–25 wt %.

When promoters are employed, they are used in quantities less than the active catalytic metal, e.g., in weight ratios of about 1/20 to 1/10 based on the active metal. (This invention also contemplates the use of ruthenium as a promoter in conjunction with cobalt as the primary active catalytic metal.) The most preferred catalysts are those containing cobalt and rhenium, cobalt and ruthenium, and cobalt and thoria, particularly cobalt and rhenium.

The catalyst can be prepared by a variety of techniques well known to those skilled in the art, including impregnation (either co-impregnation with promoters or serial impregnation—either dry or by the incipient wetness techniques). Since a preferred catalyst for fixed bed Fischer-Tropsch processes is one wherein the catalytic metals are present in the outer portion of the catalyst particle, i.e., in a layer no more than 250 microns deep, preferably no more than 200 microns deep, a preferred method of preparing the catalyst is the spray method which is described in U.S. Pat. No. 5,140,050, incorporated herein by reference or in EP 0,266,898, incorporated herein by reference. For slurry Fischer-Tropsch processes, catalysts are preferably made by incipient wetness impregnation of spray-dried supports.

Measurement of the strength of titania containing particles is not an easy task because finely divided attrition products have a tendency to adhere to the original particles and are not detectable by conventional methods, e.g., the well known Davison Attrition Test, Microtrac or Malvern light diffraction instruments. Consequently, a new accelerated attrition test was developed, wherein the results are reproducible, and based on SEM photo micrographs of attrited products is believed to operate in an erosive or grinding environment similar to the environment in large slurry, bubble column units.

The test consists of: treatment of a small sample, e.g., about 0.5 to about 3 grams, of catalyst or support suspended in acetone, and subjected to an ultrasonic bath for a prescribed period of time, and followed by filtration to quantify the amount of fines, i.e., particles less than 25 microns mean diameter, produced. Thus, 2.5 grams of sample, sieved to +45 micron size, and suspended in 12 ml acetone is charged to a 0.5 oz. bottle. After sonicating in a Branson Model 2200 ultrasonic bath, typically for thirty minutes or more, the mixture is filtered through a 500 mesh screen (25 micron openings) onto a 0.02 micron filter membrane (Whatman Anodisc). The solids are then washed with acetone, dried and weighed to determine the weight percent (wt %) <25 micron yield.

The Fischer-Tropsch synthesis is a well known process and the reaction conditions have been described in the available literature. For example, temperatures may range from about 175° to about 400° C., preferably about 180–250° C. while pressures may range from about 1–100 bar, preferably about 15 to 40 bar. Hydrogen/CO ratios may range from 0.5/1 to about 4/1, preferably about 1.7/1 to 2.5/1, with the stoichiometric amount plus or minus about 3% being most preferred. The catalyst made from the binder of this invention is preferably used in a slurry, e.g., a slurry bubble column, reactor where gas hourly space velocities may range from about 4000 to 20000. A preferred slurry bubble column operation is described in U.S. Pat. No. 5,348,982 incorporated herein by reference.

EXAMPLES

Twelve titania supports were prepared by spray-drying mixtures of various binders with Degussa P-25 TiO2. Dried supports were calcined between 700° C. and 1000° C. in rotary calciners. The amount and source of the alumina binder and of the silica binder, the wt % solids in the spray-drier feed, and the final calcination temperature, used for each of these twelve supports are summarized in Table 1. The alumina chlorhydrol sol was made by GRACE Davison, designated as CX-100, and contained about 23.5 wt % Al2O3. Analytical inspections are also shown in Table 1, including the data from 30 minute sonic attrition tests. The rutile content refers to the weight percent of the rutile phase in the titania, with the balance being the anatase phase, determined by X-ray diffraction (ASTM D 3720-78). SA refers to the BET surface area and PV refers to the pore volume of pores less than about 5000 angstroms in diameter, measured by mercury porosimetry (using a mercury contact angle of 125 degrees).

Examples 1 & 2 represent the base case with an alumina binder and possess reasonably good strength here but, as will be shown later, lose strength upon steaming. Examples 3–5 with silica sols from different commercial suppliers produced very weak particles with a high portion of fines present after calcining, indicating that the use of silica binder alone is not a viable option. Example 6 illustrates this invention with the incorporation of a binder consisting of a mixture of alumina and silica sols in 9-to-1 weight ratio. Already this support shows the lowest sonic attrition value, and hence best strength, among these unsteamed examples.

Examples 7–12 in Table 1 were calcined at 700° C. and hence contain lower rutile content in the titania, higher surface area, and higher pore volume compared to Examples 1–6. The higher pore volume is an especially important feature because more active metal can be deposited per incipient wetness impregnation as pore volume increases. Example 7, using the same mixture of alumina and silica binders as Example 6, illustrates that the significant improvement in pore volume gained at the lower calcination temperature can be achieved with only minor loss in particle strength. Comparing Example 8 with 7 indicates that changing the proportions of alumina to silica from 9:1 to 2:1, in a constant 6 wt % total binder composition, results in a good pore volume. However, higher total binder concentration, 12 wt % versus 6 wt %, gives lower pore volume, as shown by Examples 8, 9, and 12. Examples 11 and 12 illustrate that very similar results are obtained by using aluminum nitrate instead of alumina chlorhydrol sol as the source of the alumina binder.

Table 2 summarizes the inferior results obtained when silica is added to alumina-bound supports after spray-drying. Silica was added by impregnation of tetraethyl silicate from methanol solution, followed by drying and calcining at 800°

C. for 3 hours in a lab oven. As indicated in the table, much of the silicate added was lost by volatilization during the drying or calcining, which poses a serious problem for this method. More importantly, the silica that remained on the support did nothing to improve particle strength. In Example 13, addition of silica to the support of Example 1 failed to noticeably improve strength. Example 14 used a support with the same composition as Example 1, but was a much weaker starting material as a result of being recalcined at 850° C. in a static oven. Example 15 used a very weak support prepared by spray-drying an experimental, precipitated form of titania instead of Degussa P-25. In both Examples 14 & 15, the supports became even weaker after the silica addition, reflecting perhaps further weakening of the alumina binder by steaming in the calcination step. From these examples it is clear that for silica to function together with alumina as an improved binder, the two must be present in t he initial spray-drying step.

To further define credits for the new SiO2—Al2O3 binder, two Co—Re catalysts were prepared: a base case with a titania support containing 6% Al2O3 binder, and an example of this invention comprising a titania support with 6% of 9:1 Al2O3—SiO2 binder. The spray-dried supports were made similarly as in Examples 1 and 6 but on a larger scale. Each catalyst was then made by incipient wetness impregnation of an aqueous solution of cobalt nitrate and perrhenic acid, followed by air calcination at about 400° C. in a rotary calciner. Double impregnation/calcinations were applied to achieve the final metal loadings. The catalysts were tested with 2/1, H$_2$/CO synthesis gas in a small fixed bed reactor, after reduction at 375° C. Both catalysts were highly active and selective for the formation of hydrocarbons, as shown in Table 3.

The final, most critical strength test comes when subjecting the catalyst to high steam partial pressure at moderate temperature, such as that generated in hydrocarbon synthesis. To simulate this environment, portions of each catalyst were charged to a fluidized bed reactor and treated with pure steam at about 250° C., 6.8 atm pressure, for a period of six days. Fresh and steamed versions were then evaluated for attrition resistance using the sonic attrition test at a variety of sonication times. Results are summarized as Examples 16–19 in Table 4 a nd plotted in the FIGURE. Referring to the FIGURE, it is clear that the amount of fines produced in the attrition test increases with sonication times for all materials. Steaming weakens the alumina binder case, as shown by line A of data. The silica-alumina binder of this invention (line C) weakens only very slightly upon steaming, still maintaining a credit over even the unsteamed alumina case (line B). A remarkable improvement in initial strength and steam stability has been achieved with the improved binder.

TABLE 1

Spray-Dried Titania Supports

| Example | Wt % Al2O3 | Al2O3 Source | Wt % SiO2 | SiO2 Source | Wt % Solids in Spray-Dryer Feed | Calcination Temp, C | Rutile | SA | PV | Sonic Attrition |
|---|---|---|---|---|---|---|---|---|---|---|
| 1 | 6 | Chlorhydrol sol | 0 | none | 36 | 800 | 94 | 17 | 0.36 | 3.9 |
| 2 | 6 | Chlorhydrol sol | 0 | none | 36 | 800 | 95 | 14 | 0.34 | 3.6 |
| 3 | 0 | none | 6 | Nyacol 2034 D.I. | 23 | | 83 | 20 | 0.28 | — |
| 4 | 0 | none | 6 | Nalco 2327 | 20 | | 87 | 17 | 0.30 | — |
| 5 | 0 | none | 6 | Nalco 1034A | 20 | | 92 | 17 | 0.30 | 10.5 |
| 6 | 5.4 | Chlorhydrol sol | 0.6 | Nyacol 2034 D.I. | 36 | 1000 | 93 | 17 | 0.33 | 1.1 |
| 7 | 5.4 | Chlorhydrol sol | 0.6 | Nyacol 2034 D.I. | 36 | 700 | 16 | 44 | 0.54 | 3.2 |
| 8 | 4 | Chlorhydrol sol | 2 | Nyacol 2034 D.I. | 36 | 700 | 14 | 51 | 0.50 | — |
| 9 | 10.8 | Chlorhydrol sol | 1.2 | Nyacol 2034 D.I. | | 700 | 14 | 52 | 0.37 | — |
| 10 | 8 | Chlorhydrol sol | 4 | Nyacol 2034 D.I. | | 700 | 15 | 55 | 0.38 | — |
| 11 | 5.4 | Aluminum nitrate | 0.6 | Nyacol 2034 D.I. | | 700 | 14 | 50 | 0.47 | — |
| 12 | 10.8 | Aluminum nitrate | 1.2 | Nyacol 2034 D.I. | | 700 | 13 | 55 | 0.35 | — |

TABLE 2

ADDITION OF SILICA TO SUPPORTS WITH ALUMINA BINDERS

| Example | Wt % SiO2 Added | Wt % SiO2 Found | Sonic Attrition Before SiO2 Added | Sonic Attrition After SiO2 Added |
|---|---|---|---|---|
| 13 | 0.6 | 0.13 | 3.9 | 3.2 |
| 14 | 0.6 | 0.13 | 14.7 | 30.4 |
| 15 | 0.6 | 0.21 | 37.6 | 46.1 |

TABLE 3

HCS TESTS OF CATALYSTS WITH ALUMINA AND SILICA-ALUMINA BOUND SUPPORTS
200° C., 280 psig, 64%H2-32%CO-4%He

| Binder | Al2O3 | 9:1 Al2O3-SiO2 |
|---|---|---|
| Wt % Co | 12.0 | 10.6 |
| Wt % Re | 1.0 | 0.9 |
| Bulk Density, g/cc | 1.33 | 1.47 |
| GHSV | 3000 | 3000 |
| % CO conversion | 66 | 77 |
| Mol % CH4 | 6.6 | 5.6 |

TABLE 4

EFFECT OF STEAMING ON CATALYST ATTRITION

| | | | Sonic Attrition Test | |
|---|---|---|---|---|
| Example | Binder | Treat | Minutes | Wt % 25- |
| 16 | Al2O3 | Fresh | 0 | 0.2 |
| | | | 10 | 0.4 |
| | | | 20 | 0.7 |
| | | | 20 | 0.9 |
| | | | 30 | 3.6 |
| | | | 40 | 3.8 |
| | | | 60 | 8.5 |

TABLE 4-continued

EFFECT OF STEAMING ON CATALYST ATTRITION

| Example | Binder | Treat | Sonic Attrition Test Minutes | Wt % 25- |
|---------|--------|-------|---------|----------|
|         |        |       | 90      | 7.0      |
|         |        |       | 90      | 6.3      |
| 17      | Al2O3  | Steamed 6 days | 0  | 0.7 |
|         |        |       | 10      | 5.0      |
|         |        |       | 20      | 5.4      |
|         |        |       | 20      | 6.2      |
|         |        |       | 30      | 7.4      |
|         |        |       | 30      | 12.0     |
|         |        |       | 40      | 11.6     |
|         |        |       | 60      | 18.5     |
|         |        |       | 90      | 22.1     |
|         |        |       | 120     | 28.4     |
| 18      | SiO2-Al2O3 | Fresh | 30  | 0.4      |
|         |        |       | 30      | 0.5      |
|         |        |       | 60      | 1.3      |
|         |        |       | 120     | 1.1      |
|         |        |       | 120     | 1.9      |
| 19      | SiO2-Al2O3 | Steamed 6 days | 30 | 1.1 |
|         |        |       | 30      | 1.4      |
|         |        |       | 30      | 2.3      |
|         |        |       | 60      | 2.7      |
|         |        |       | 60      | 4.5      |
|         |        |       | 120     | 6.6      |
|         |        |       | 120     | 8.8      |

We claim:

1. A Fischer-Tropsch process for the reaction of synthesis gas comprised of hydrogen and carbon monoxide which process comprises reacting the synthesis gas over a supported catalyst containing a Group VIII metal, the support comprising a particulate, primarily titania support with which there is incorporated a binder comprised of silica and alumina, wherein support particles have a size range of about 20 to 120 microns, and the binder is less than 30 wt % of the support.

2. The process of claim 1 wherein the silica is less than about 50 wt % of the binder.

3. The process of claim 1 wherein the support is at least about 80% titania.

4. The process of claim 2 wherein the binder is about 3–20 wt % of the support and the silica is about 3 to less than 50 wt % of the binder.

5. The process according to any one of claims 1–4 wherein the Group VIII metal is selected from the group consisting of cobalt, ruthenium and mixtures thereof.

6. The process of claim 5 wherein the Group VIII metal is promoted with a metal selected from the group consisting of rhenium, hafnium, zirconium, cerium, thorium, and uranium.

7. The process of claim 6 wherein the promoter metal is rhenium.

8. The process of claim 5 wherein the process is conducted in a slurry.

9. The process of claim 8 wherein the temperature is about 175–400° C.

10. The process of claim 8 wherein the process is conducted in a slurry bubble column.

* * * * *